US011040122B2

(12) United States Patent
Samain et al.

(10) Patent No.: US 11,040,122 B2
(45) Date of Patent: Jun. 22, 2021

(54) DEVICE AND SYSTEM FOR DISPENSING CUSTOMIZED SCENTS

(71) Applicant: L'Oreal, Paris (FR)

(72) Inventors: Henri Samain, Bievres (FR); Franck Giron, Lagny sur Marne (FR)

(73) Assignee: L'Oreal, Paris (FR)

( * ) Notice: Subject to any disclaimer, the term of this patent is extended or adjusted under 35 U.S.C. 154(b) by 327 days.

(21) Appl. No.: 16/151,411

(22) Filed: Oct. 4, 2018

(65) Prior Publication Data

US 2020/0108164 A1    Apr. 9, 2020

(51) Int. Cl.
*A61L 9/12* (2006.01)
*A61L 9/14* (2006.01)

(52) U.S. Cl.
CPC ............. *A61L 9/125* (2013.01); *A61L 9/14* (2013.01)

(58) Field of Classification Search
CPC .................................. A61L 9/14; A61L 9/125
See application file for complete search history.

(56) References Cited

U.S. PATENT DOCUMENTS

| 2017/0360178 A1 | 12/2017 | Samain et al. |
| 2020/0077767 A1* | 3/2020 | Artal Lahoz .......... A45D 34/02 |
| 2020/0276549 A1* | 9/2020 | Jedlinski ............. B01F 15/0237 |

FOREIGN PATENT DOCUMENTS

WO    WO-2016087469 A1 *  6/2016  ......... A45D 40/0075

OTHER PUBLICATIONS

International Search Report and Written Opinion dated Dec. 16, 2019, in PCT/IB2019/001046, 13 pages.

* cited by examiner

*Primary Examiner* — Sean E Conley
(74) *Attorney, Agent, or Firm* — Oblon, McClelland, Maier & Neustadt, L.L.P.

(57) ABSTRACT

A scent dispensing device is provided that includes a plurality of containers, each containing a different scent ingredient; a driving system configured to separately cause each of the plurality of containers to dispense a quantity of the respective scent ingredient; and a delivery system configured to transport any dispensed quantities from the scent containers to a common receiving area for dispensing onto to a single medium.

14 Claims, 12 Drawing Sheets

To change the scent cartridges, the top is pushed down by the user. Then, it automatically goes up (spring effect) and the user has to turn a little to have access to the cartridges.

DEVICE AND SYSTEM FOR DISPENSING CUSTOMIZED SCENTS

BACKGROUND

Field of Invention

The present application relates to a system for allowing a user to imagine, create, improve, and test a recipe of perfume.

SUMMARY

In an embodiment, a scent dispensing device is provided, comprising: a plurality of containers, each containing a different scent ingredient; a driving system configured to separately cause each of the plurality of containers to dispense a quantity of the respective scent ingredient; a delivery system configured to transport any dispensed quantities from the scent containers to a common receiving area for dispensing onto to a single medium.

In an embodiment, the dispensed quantity of each unitary drop of the respective scent ingredient is less than or equal to 2 µL.

In an embodiment, the dispensed quantity of each unitary drop of the respective scent ingredient is greater than 2 µL, such as less than or equal to 4 µL, or less than or equal to 2=10 µL.

In an embodiment, a total quantity of the dispensed quantity of the respective scent ingredients onto the single medium is less than 200 µL.

In an embodiment, the driving system includes an electric motor that drives a gearhead which pushes a piston to dispense a quantity of a scent in the respective container.

In an embodiment, an encoder is coupled to the electric motor and is configured to count step movements of the gearhead, wherein the electric motor controls the dispensing of the quantity of the scent based on the count detected by the encoder.

In an embodiment, the encoder is configured to detect a total quantity of the scent dispensed by the respective container based on an amount of step movements that have been performed by the gearhead.

In an embodiment, a movement of the piston causes an amount of the scent liquid to be pushed through a capillary which is connected to a tube which leads to the common receiving area.

In an embodiment, an internal diameter of the tube is between 0.5 mm and 3 mm.

In an embodiment, an internal diameter of the tube is between 0.7 mm-1 mm.

In an embodiment, a system is provided comprising: a user terminal configured to receive an input of a recipe to form a scent based on one or more quantities of different scents chosen from a plurality of different scent ingredients; and a scent dispensing device that includes: a communication interface configured to receive the recipe from the user terminal, a plurality of containers, each containing one of the plurality of different scent ingredients; wherein the scent dispensing device is configured to separately cause the plurality of containers to dispense a quantity of a respective scent ingredient onto a single medium according to the recipe.

In an embodiment, after the plurality of containers dispense the quantity of a respective scent ingredient onto the single medium according to the recipe, the user interface is configured to allow the user to revise the recipe.

In an embodiment, after the plurality of containers dispense the quantity of a respective scent ingredient onto the single medium according to the recipe, the user interface is configured to allow the user or manager of the system to store the recipe into a memory.

In an embodiment, after the plurality of containers dispense the quantity of a respective scent ingredient onto the single medium according to the recipe, the user interface is configured to allow the user to request a large volume bottle of perfume be created according to the recipe.

In an embodiment, after the plurality of containers dispense the quantity of a respective scent ingredient onto the single medium according to the recipe, the user interface is configured to allow the user to provide feedback regarding the user's opinion of the created scent.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION

Figure 1:
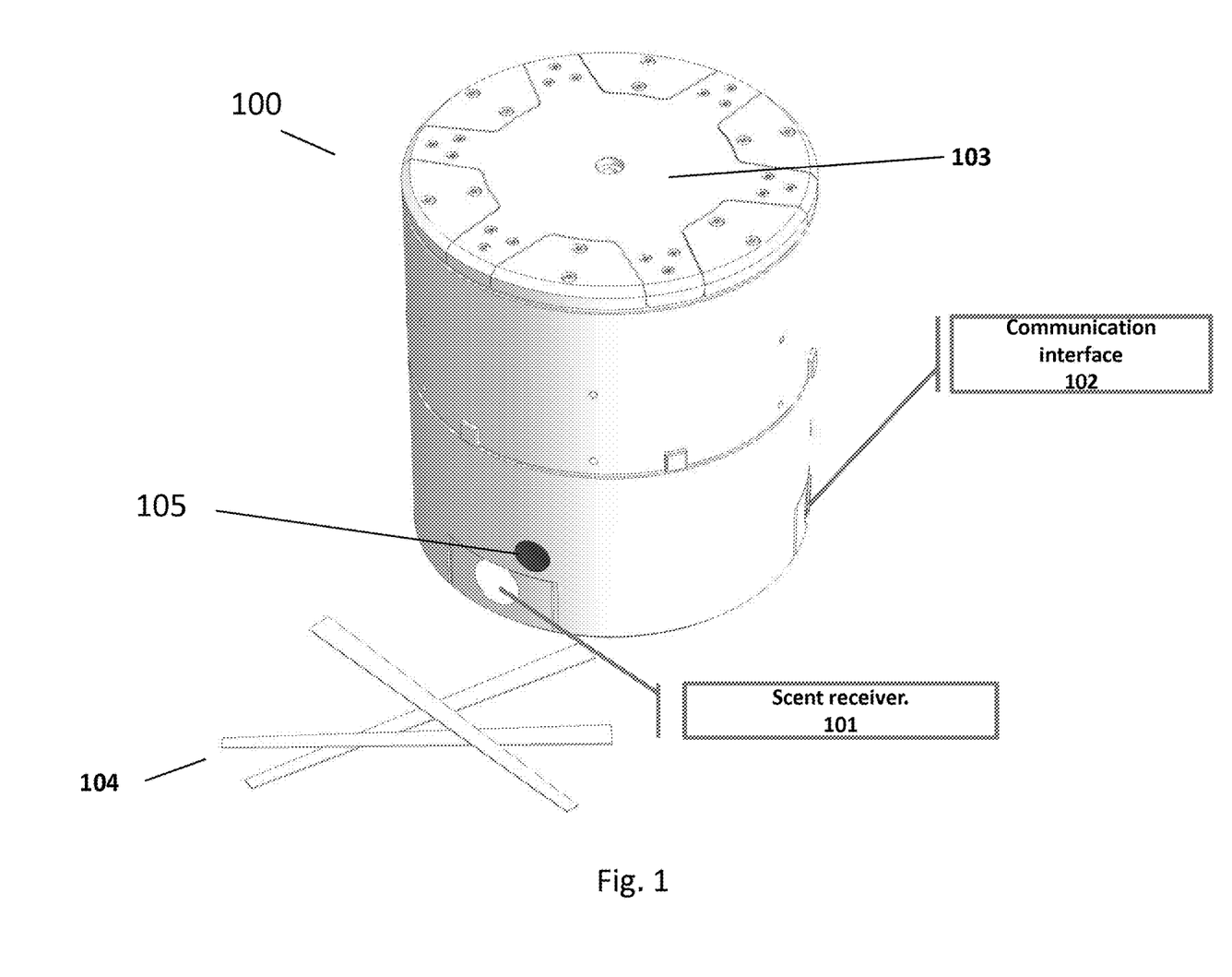
FIG. 1 shows a scent dispensing device according to an embodiment.

FIG. 1 shows a scent dispensing device 100 according to an embodiment. The scent dispensing device is configure to dispense a small amount of fragrance/scent ingredient from scent receiver 101 which is presented as an opening in the exterior housing of the device. The device 100 also may include a communication interface, which is shown as a Universal Serial Bus (USB) interface in FIG. 1, but it may be another type of communication interface, as will be described below. The device 100 includes a cover 103 which allows access to the scent containers when released (see FIG. 4 below). Also shown are paper strips 104, which may be inserted into the scent receiver area 101, however, other items may be inserted to receive the scent drops, such as a user's finger or a container. The exterior housing includes one or more buttons 105 for opening the exterior housing cover to access the internal components of the device.

A system, which includes the device 100 is based on several scent containers and very precise dispensers able to create perfume samples at the level of 100-200 µL, and functions to help users to create and progress in perfume. The system enables a user to try different blends and back and forth to arrive to satisfactory recipe in few minutes and without any effort. It is noted that while the term "user" is commonly used throughout this specification, this may refer to a customer, employee, manager, or any other position with respect to the location of the system. The system further enables an understanding of the tastes of different users.

As will be discussed below, the device 100 may include
- 6 (or more) scents
- 6 high precision dispensers
- Able to make blends at the level of drops (100 µL)
- Unitary drop (example precision)=2 pt. The unitary drop precision is not limited to this example, and may be larger such as on the order of equal to or less than 4 µL, or even equal to or less than 10 µL.

Each container delivers their drops in the same area but separately (distance between ends is around 1 mm). The containers are designed so that there is no risk of pollution or contamination from one dispenser to another.

Figure 2:
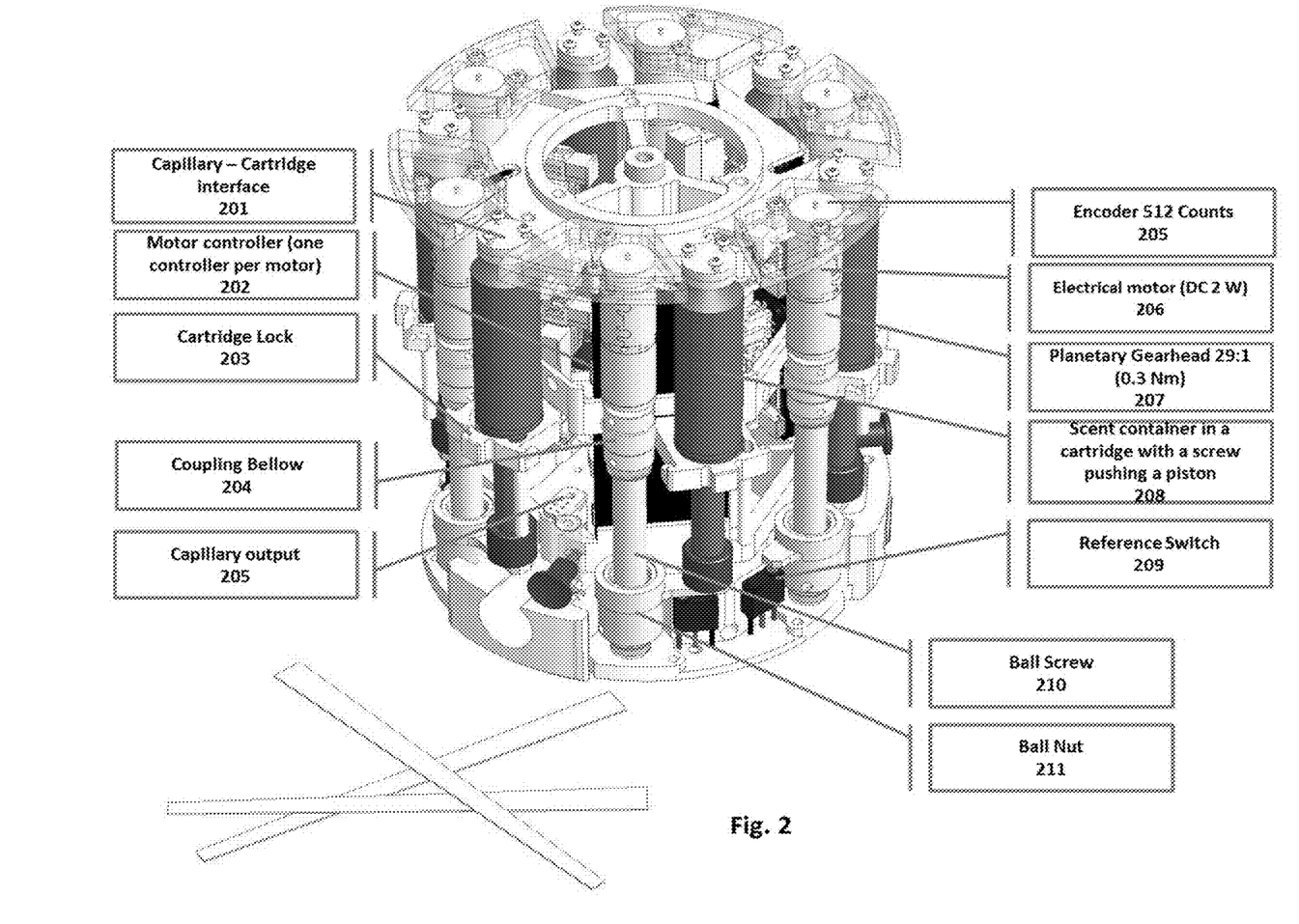
FIGS. 2-3 each show a detailed view of the inside of the dispensing device according to an embodiment.

FIG. 2 shows a detailed view of the inside of the device 100. The device includes scent containers 208 as mentioned above. The scent containers are in cartridge form and are configured to be dispensed with a screw pushing a piston. Preferably, the diameter doesn't exceed 20 mm, and more preferably is comprised between 5 to 18 mm. In case containers with different volumes are needed, the system should keep the diameters in the same range as defined above, but the height of the containers may be adapted according to volume needs. The containers' height may be between 1 cm to 1 m, and preferably between 4 cm and 20 cm. FIG. 2 shows six scent containers disposed in a radial fashion around a center axis of the device 200, but more or less scent containers may be used. While the arrangement of the containers is shown in a radial manner, other arrangements are possible.

The device 100 further includes an electric motor 206 that drives a planetary gearhead 207. The gearhead 207 is coupled to a ball screw 210 and a ball nut 211, via a coupling bellow 204, which turn are coupled to the screw which pushes the piston of the scent container in an upward direction, so that turning the gearhead causes vertical movement of the screw against the piston to dispense a certain amount of the scent.

An encoder 205 that is coupled to the motor 206 can precisely count the step movements of the gearhead to ensure a precise dispensing operation. A quantity of scent is checked by the device to warn when a container is low. This is accomplished by checking the amount of dispensing that has been performed based on the encoder 205 detecting the amount of step movements that have been performed by the gearhead and reporting the data to the micro controller.

Reference switch 209 is configured to initialize the encoders at a start of receiving a new container.

A motor controller 202 is provided for each motor 206 to actuate the motor with control signals.

Each scent container is held in place by a cartridge lock 203. The movement of the piston of the container causes an amount of the scent liquid to be pushed through a capillary at a cartridge interface 201. The capillaries interfacing with each scent container lead to a capillary output 205 which releases the liquid drops into the scent receiver 101 (shown in FIG. 1).

Figure 3:
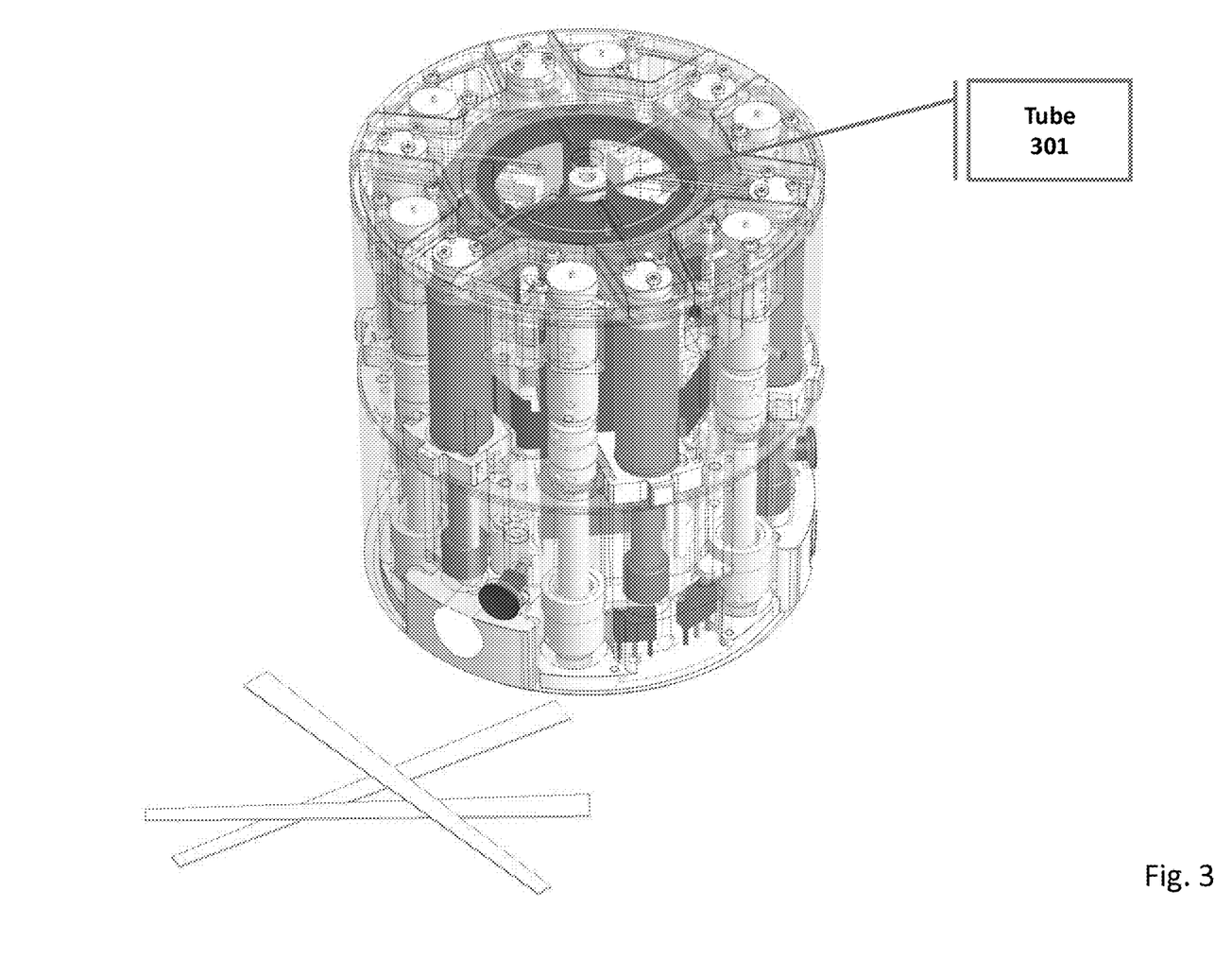

FIG. 3 shows that each capillary is connected to a tube 301 which leads to the center axis of the dispenser, and then to the capillary output 205. The internal diameter of the tube 301 is small but not too small in order not to create too high pressure loss. Preferably, the internal diameter is higher than 0.5 mm, and more preferably higher than 0.6 mm. It can be larger but it should not be too high in order to avoid vacant space. Thus, preferably the internal diameter should not exceed 3 mm. Preferably, the internal diameter is in the range of 0.7 mm-1 mm. The six tubes go down just above the chamber, allowing that drops can fall down on the paper (or a container, finger, etc.). The length of the tube can be in the range of few centimeters to few decimeters and should not exceed 1 m.

Figure 4:
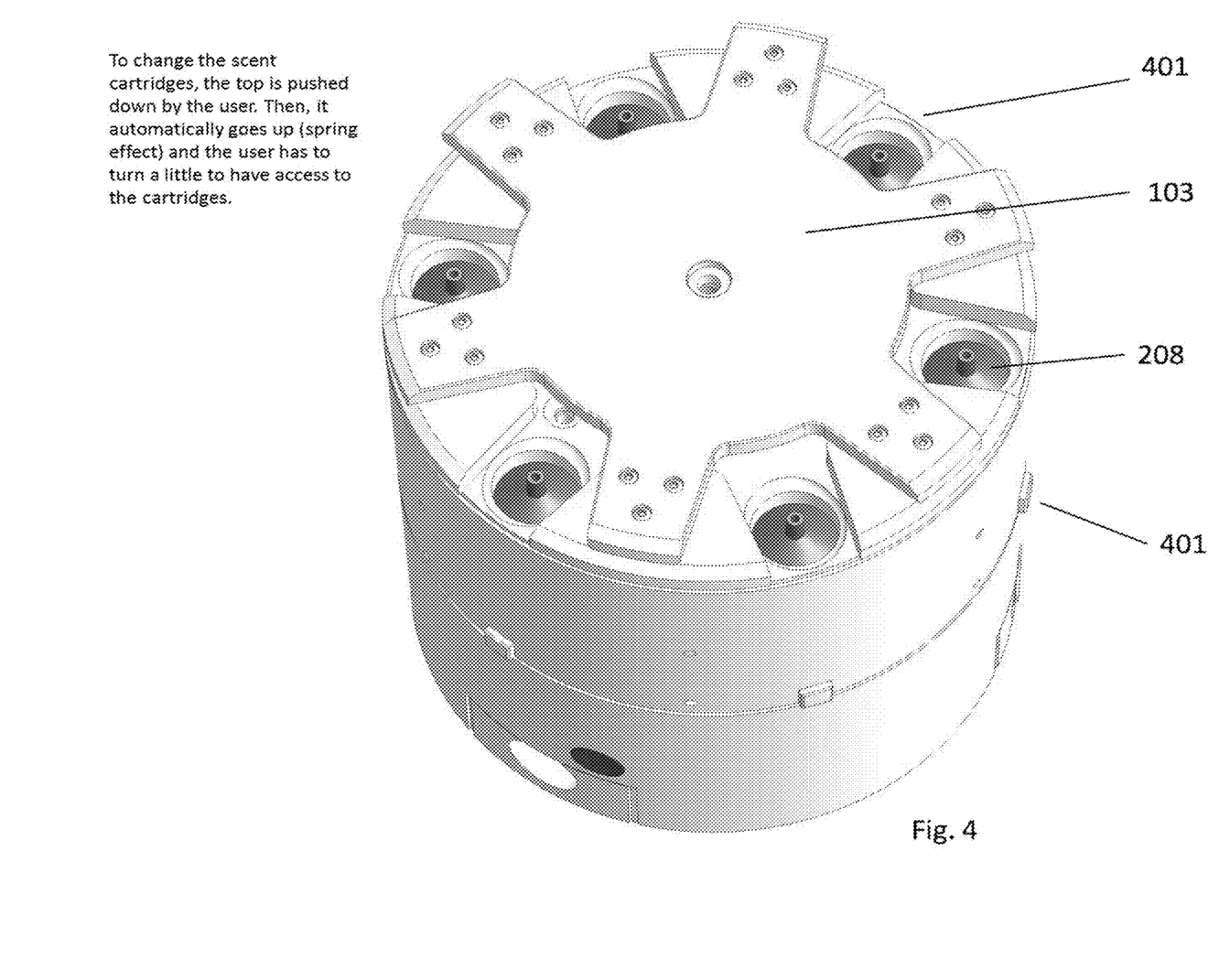
FIG. 4 shows a top view of the dispensing device when the cover is released according to an embodiment.

FIG. 4 shows a top view of the device 100 when the cover 103 is released. To change the scent cartridges, the top is of the cover 103 is pushed down by the user. Then, cover 103 automatically rises (spring effect) and the user may manually turn a rotate the cover to reveal the opening 401 access to the scent container cartridges 208. Once the cover 103 is in the position shown in FIG. 4, by pushing any of the six buttons 402, cartridges are released, and can be removed and changed.

Figure 5A:
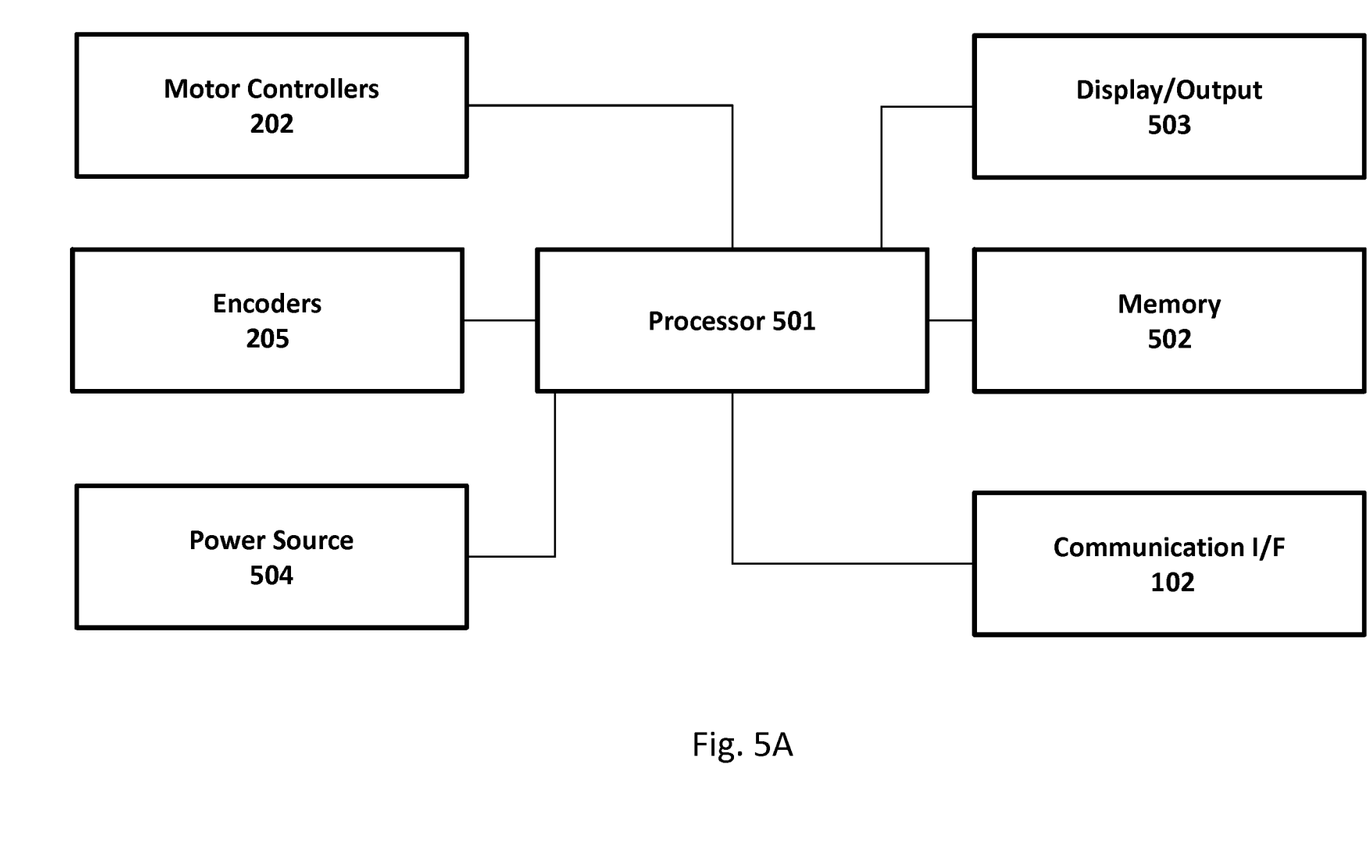
FIGS. 5A-5B show hardware diagram s of the dispensing device according to different embodiments.

FIG. 5A shows a hardware diagram of the device 100 according to an embodiment. The device 100 may include a processor 501, a memory 502, an optional display or output indicator 503, and a power source 504. These elements are in addition to the communication interface 102, the motor controllers 202, and the encoder 205 already discussed above.

The hardware can be designed for reduced size. For example, the processor 501 may be a CPU or microcontroller as understood in the art. For example, the processor may be an APL0778 from Apple Inc., or may be other processor types that would be recognized by one of ordinary skill in the art. Alternatively, the CPU may be implemented on an FPGA, ASIC, PLD or using discrete logic circuits, as one of ordinary skill in the art would recognize. Further, the CPU may be implemented as multiple processors cooperatively working in parallel to perform the instructions of the inventive processes described above.

Further, the communication interface (I/F) 102 can include circuitry and hardware for communication with a user terminal as will be discussed below. The communication interface 102 may be a universal serial bus (USB) interface, or it may include a network controller such as BCM43342 Wi-Fi, Frequency Modulation, and Bluetooth combo chip from Broadcom, for interfacing with a network.

Figure 5B:
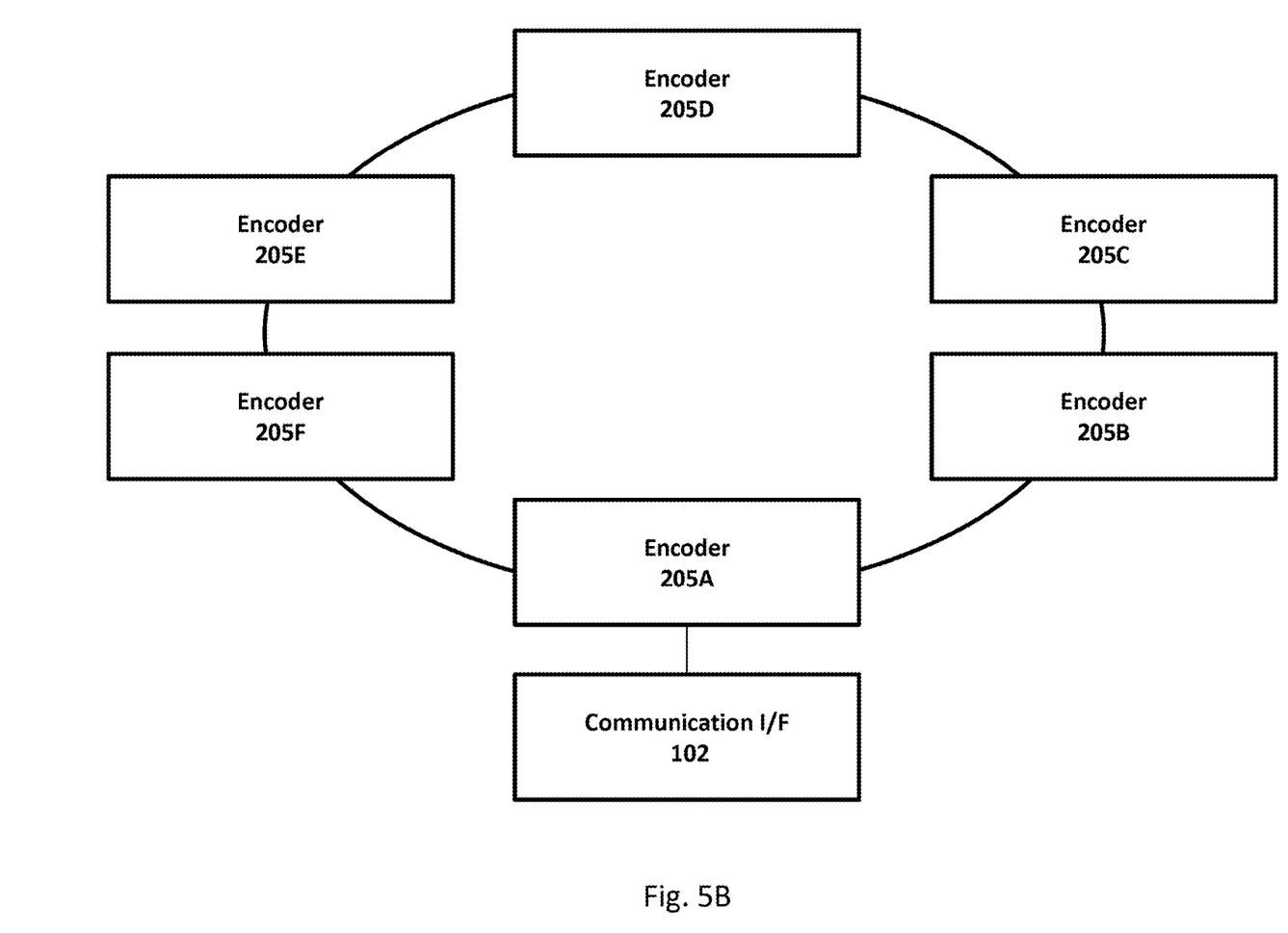

Alternatively, as shown in FIG. 5B the processor 501 is not required to centrally coordinate the functionality and control of the device 100. In this case, the solution is based on the circuitry of the 6 encoders 205A-F. One of the six encoders (205A) receives the communication from the communication interface 102, and then acts as a hub for the other five encoders. The six are connected as a chain operating under a local addressing protocol such that each encoder understands which encoder is destination of any received instructions.

According to an embodiment, the device 100 can be used to test blends of various scents easily and instantly while using a small quantity (100 µL). It enables a user to try, test, and retry to go back and forth to a creation of a preferred scent.

Figure 6:
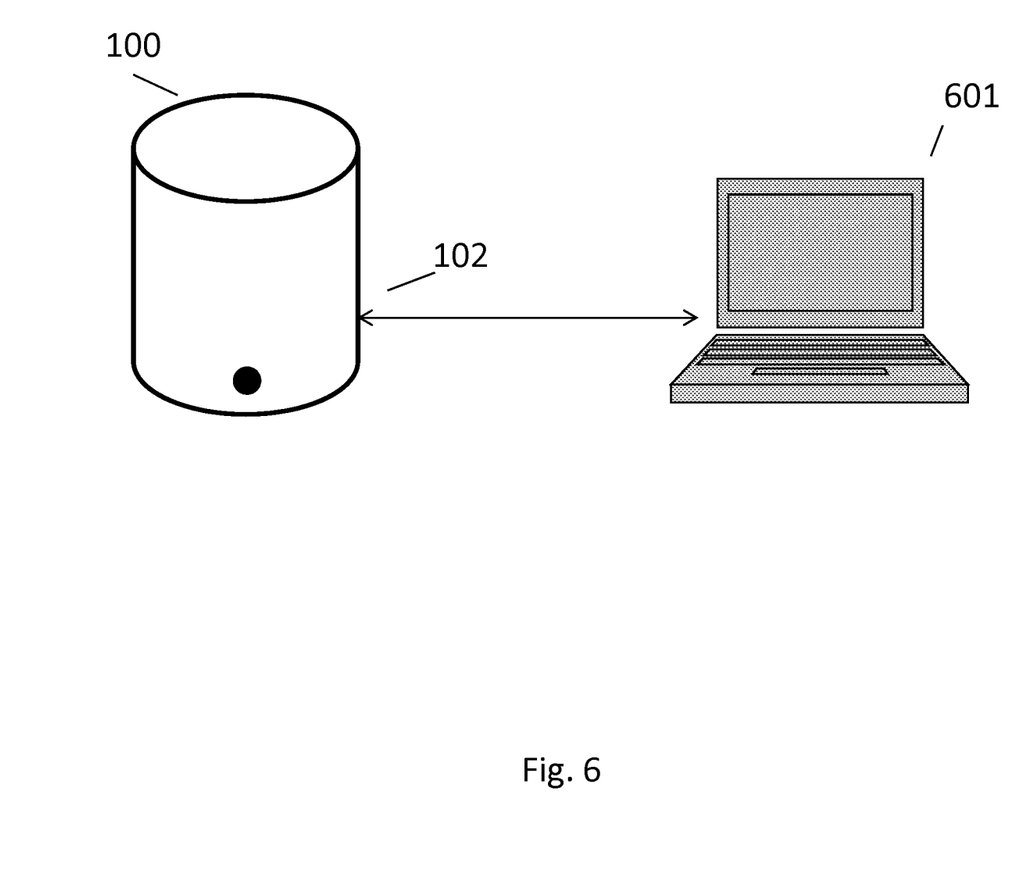
FIG. 6 shows a system that includes the dispensing device and a user terminal according to an embodiment.

FIG. 6 shows that the device 100 may be connected to a user terminal 601 via the communication interface 102. The combination of the device 100 and the user terminal may be considered to be part of a "system."

Figure 7:
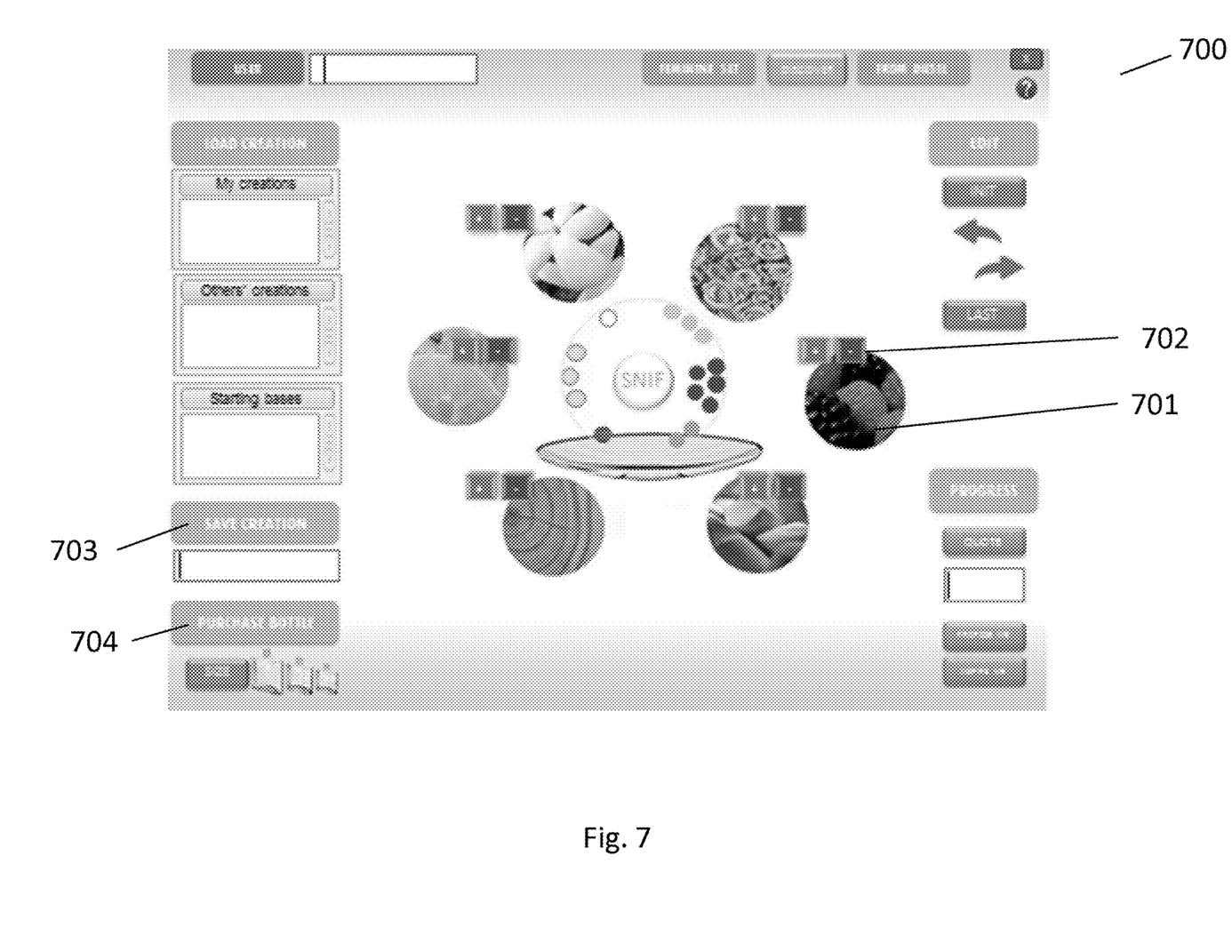
FIG. 7 shows a user interface for the dispensing according to an embodiment.

FIG. 7 shows a user interface 700 for the device 100 that is displayed on the user terminal 601 after the user terminal establishes a connection with the device 100. The interface allows creation of a recipe on a display screen. The screen may display scents 701 as an image (such as a fruit, flower, etc.) to invoke the type of scent. Buttons 702 may be used to add or increase the number of drops of each scent. After various quantities of one or more of the scents contained in the device 100 are selected, the user may provide an input to the "SNIF" button to cause the combined scent to dispense from the device 100. The user then may revise the recipe (after sniffing) using same buttons described above. The user may store the recipe in memory at button 703 ("save creation"). Also, the system may store all the past recipes that have been made/tried. The user may try to purchase the scent at 704. Such a purchase can be made by transmitting the recipe to a manufacturer or seller who can custom make a bottle according to the recipe. In this regard, another machine can be used to create custom bottle based on programmable dispensers. A printing of the recipe can also be ordered.

The device 100 or the user terminal 601 may store basic data such as certain predetermined recipes. The system can have tutorials to explain each scents and rules to follow for the blending. During explaining the scents, the system can make deliver them in order the client understands better (by a quotation and/or by a ranking)

Figure 8:
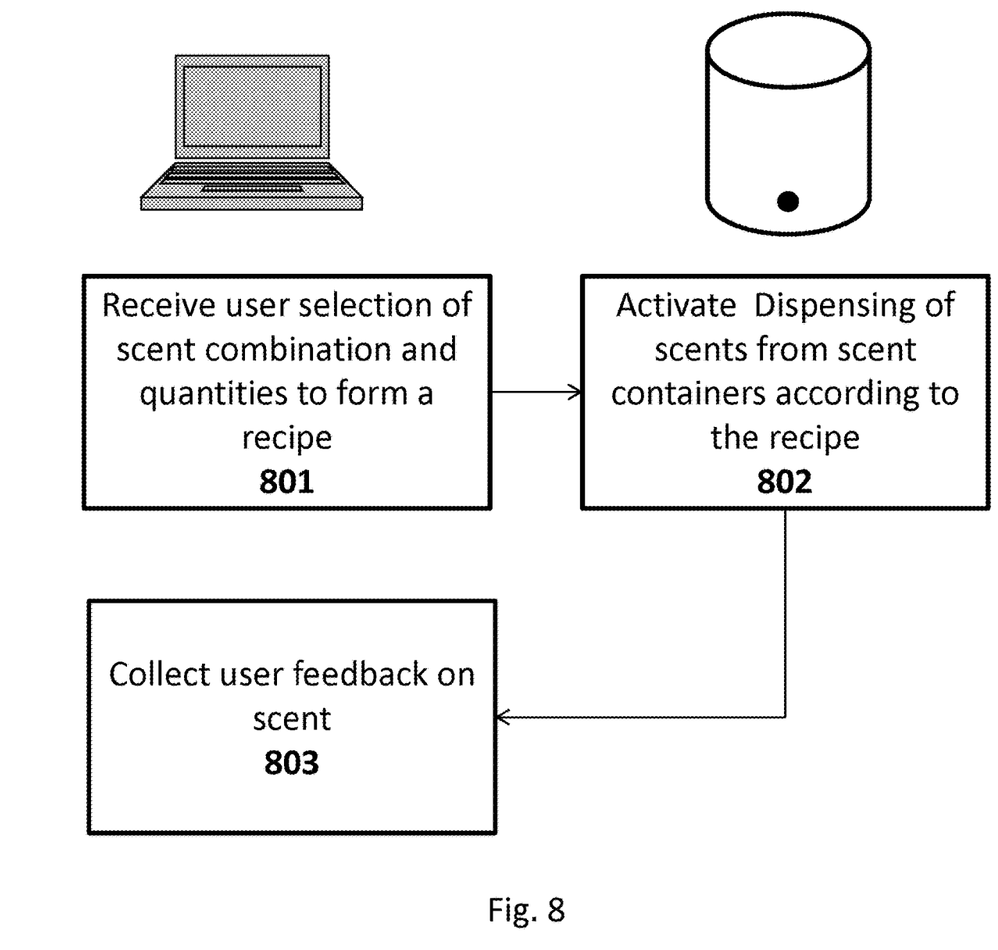
FIG. 8 shows a basic process performed by the system which includes the dispensing device and the user terminal according to an embodiment.

FIG. 8 shows a basic process performed by the system which includes the scent dispensing device 100 and the user terminal 602. At step 801, the user terminal 601 receives a user selection of scent combination and quantities to form a recipe. This step may be performed by the operations on the user interface describe above. The user terminal then transmits the recipe to the device 100, and then at step 802, the device 100 activates dispensing of scents from scent containers, according to the recipe, onto a medium such as paper, a user's finger, or a container. Next, an optional step 803 may be performed where the user terminal receives feedback from the user regarding the dispensed scent(s). This feedback may take many forms as will be described below. Additionally, the feedback is not necessarily performed at the user terminal 102, and it may be performed on a separate device (such as the user's smartphone) and uploaded to a commercial server (such as a cloud server).

[Advanced Functions for Utlizing the Dispensing Device]

While the above describes the basic structure and operation of the scent dispensing device 100, the advantage the device provides for easily creating perfume scent samples in small doses leads to innovations in determining user perfume preferences at the individual level and over multiple users. This functionality will be described below.

The system may include advanced functions, such as a procedure for beginning a session with a user. The system can propose a session to understand the tastes and wishes of the client, or to understand if the client can be classed in one or another classification of clients). Based on the session, the system may deduce the best scents to use.

For instance, a questionnaire may be given to user which asks for personal information, such as age, habits, favorite foods. The questionnaire may ask the user for their preferred and disliked commercialized perfumes, and further ask what is liked and not liked in these (in terms of notes, level of strength, level of lasting).

A combination of the scents contained in the device 100 may be referred to as a "rack." Using a given rack, the system can propose a session to understand the tastes and wishes of the client. It may propose to begin with:

A "preloaded recipe" to be used as pre-recipe

An original recipe that the system creates, to be used as pre-recipe

Advice (such as: "you should use scent X as main and scent Y as auxiliary . . . ")

The system can use the information and conversion tables to deduce a rack, pre-recipes or advice, such as:

By automatic programs. For instance, if the user may like several blends, the system can make a calculation of an "intermediate" recipe or "extrapolated" recipe.

By help of humans. For instance, an expert can deduce from the answers a recipe to propose.

The system may ask if the user is a "beginner" to using the device 100 and then propose help for the session. In particular, it can ask to activate functions like to "quotation" or "automatic advice."

The system may include advanced functions, such as an automatic helping function." During tests and sniffs, system can propose frequent Questions and Answers (i.e.: Q=what to do if the blend is too sweet. A=avoid using scents X and Y together). The proposal can be targeted if the system interprets a particular disequilibrium.

The system may propose to return to one recipe if the client is far from what is expected through the questionnaire. The system will identify among the different recipes done so far the one that is the most appropriate During tests and sniffs, the system can detect if the client feels lost (i.e. for instance, if the client comes from a recipe to another without logic) (or if the client takes more and more time to go from a sniff to another). In this case, the system can then select few of the recipes (the ones identified as the most different) and then make the client sniff again. The system may propose to activate the quotation function. The system may propose particular protocols, such as asking the user to stop and resume another time; ask for an expert; resume from scratch; or come back to the questionnaire.

During tests and sniffs, the system can detect if the client makes always the same blends. In this case, it can then propose to explore other blends or it can propose to activate the quotation function.

During tests and sniffs, system can detect if the client comes back often to a same group of blend or use always a specific scent. In this case, the system can then propose pre-recipe based on this group or this scent An advanced function mentioned above, is the use of a "quotation." During tests and sniffs, the client may quote his/her creation (can be a note and note+comments). In this case, the system may use the data to identify among the different recipes done so far the one that is the best quoted. It can propose to come back on the "best three": Sniff again, propose help around these ones. The system may detect the case of most of the quotations are bad, and then propose different actions, such as asking the user to stop and resume another time; ask for an expert; resume from scratch; or come back to the questionnaire.

The system may use the data to identify other clients that had the same tastes and then propose to work on their "best recipe" (i.e. if a client A creates a recipe and provided a good quotation, and the system detects that another client B did the same recipe and also made a similar quotation, then the system can propose to the client A the best formula of client B). The same can be done on the base of bad quotation. (i.e. if a client A does a recipe and provided a bad quotation, and the system detects that another client B did the same recipe and made a bad quotation, then the system can propose to the client A the best formula of client B).

The system may use the data to make a profile of the client and compare to other profiles to propose different specific directions to propose a series of best proposals.

During tests and sniffs, the system may detect that the client does not provide a quotation. In this case, the system may request a quotation, or it may propose to reproduce the blends (the most significantly different) and then request the client to provide a quotation.

Also contained in the advanced functions of the system are steps for finalizing the session. At the end of a session, or when a quotation appears high, the system may:
propose to test on the skin;
provide the user an option to ask friends what they think;
propose to make a mini-sample to take home; or
propose for the user to wear it the day and decide later on a next action.

At the end of the session, when the client is happy with her creation, the client or the system can propose to store a recipe in the memory of the system. The system has a memory and can store the recipe under the user's name.

The user may ask or the system can propose for a bottle for the user or another person as a gift. The system can send the recipe to a human or to a machine for the preparation of the bottle. The client can give or the system can propose to give rights to others to use her recipe (it can be limited to a selection of friends). The system sends the data to a server.

The user may ask for or the system to propose a series of variations of the recipe (i.e. a spicy one, a sweet one . . . ). The system can make automatically proposals to sniff in the moment, or, send a proposal afterwards to the client.

At the end of the session, if the client is not perfectly happy with her creation, the use can ask for someone to finalize her blends. For that, the system will ask which of her blends, she wants to be finalized. She can identify one or another, or ask the specialist to choose the blend to work on. She can allow the specialist to use the questionnaire data to do this work.

In any case (happy or not happy), the client can resume her work in another session and all data can be stored in order to be able to reuse all blends to work again. The system may propose for other users to quote one client's recipe. The system may open a group for co-design, as follows.
The group can be created randomly
The group can be created on a logic of questionnaire
The group can be created on a logic of accordance of quotations
The group can be created on a logic on discordance of questionnaire or quotations
The group can integrate a specialist
Each user the group has the possibility to provide a quotation and create on the base of one or more recipe. The system can also make calculation on the blends and propose to the group to quote and create. The system may provide a user a list of blends already done by her or others or selection of others, or warn the user if she goes in a direction already tested by her or others or selection of others.

The system can identify that certain recipes are well appreciated and put them in the preloaded library. The system may deduce the scents that are less or more used for optimizing the rack. The system can identify that certain recipes are original and put them in the preloaded library.

The system may also identify users that create blends that most users also create, or users that create blends that are very original. In that case, the system can propose that these "special clients" become creators or co-creators, or testers of commercial perfume products.

The system can progress the rack (update the types of scents in the device), by proposing to a client to do another session by changing the rack with new scents (such as 6 new scents). The system can propose to do another session by using a rack using certain new scents while keeping scents already used. For instance:
The client can select or the system can propose to select the scents that were the most appreciated during previous sessions (i.e. 4 of the 6) and the system can propose to add new scents (2)
The client can ask or the system can propose to use one or more recipes as "one" of the scent
The client can ask or the system can propose to combine two or more scents in one and then let a new place for additional scents
The client can ask or the system can propose to deconvolute one scent into two scents (i.e. if one scent contains orange and lemon, the system can propose to have one scent with orange and one with lemon, in order to let the client choose the best proportions)
The client can ask or the system can propose to change the formula of one scent to make it more appropriate (i.e. I want to keep citrus, but less bitter)

The system may make a calculation on different wishes of clients to identify the best rack to offer. A new rack can be open or limited to a group.

The system may perform an advanced learning function. The system may store the quotations of one client in a matrix in X dimensions (X=number of scents. If the client has worked only with one rack, X=6. If he/she worked on several racks, X>6). From this matrix, the system can deduce:
The best appreciated blends
The best appreciated scents
The best combination of scents
The blends that were not tested
The scents that were not tested
The racks that were not tested
From these results, the system may propose:
Commercial products which odor is close to the best appreciated blends
Commercial products which use the best appreciated scents
Commercial products which uses the best combination of scents
The client to test blends that were not tested
The client to test scents that were not tested
The client to test Racks that were not tested
By comparison of Matrixes of different clients, we can deduct:
Group of clients that seems to have the same appreciation and use this to select products to propose
Propose to ones the product (cosmetic or not) that others like Regarding the role of scents, it is noted that a "note" may be equivalent in role to a scent. Each of the 6 scents may be a note or a combination of notes. Some scents can be top note, others can be heart note, others can be base note. Each of the 6 scents can be a combination of notes with equilibrium (top note+heart note+base note).

Figure 9:
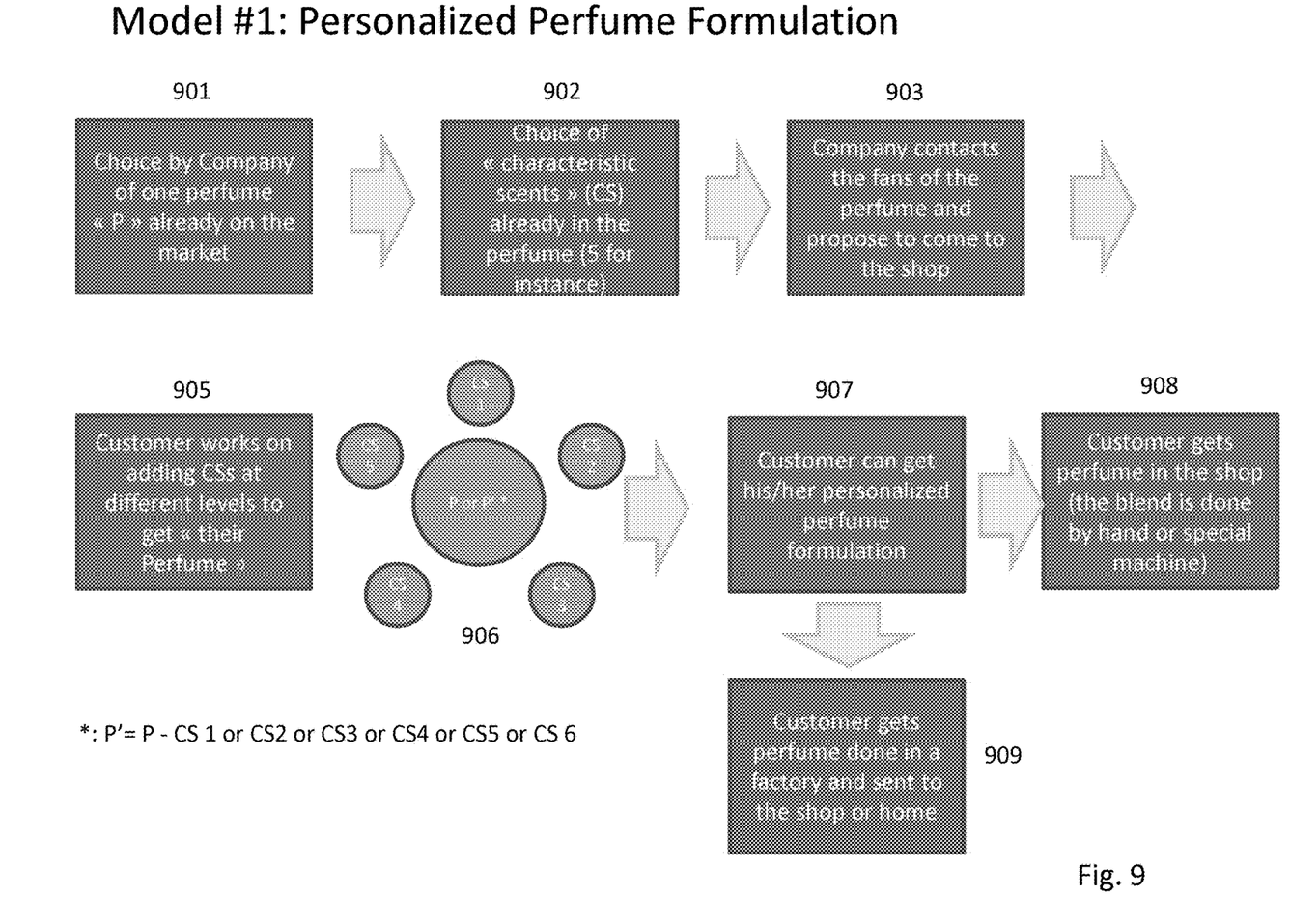
FIGS. 9-11 show examples methodologies which utilized the dispensing device to create a personalized perfume or a new perfume product according to different embodiments.
Figure 10:
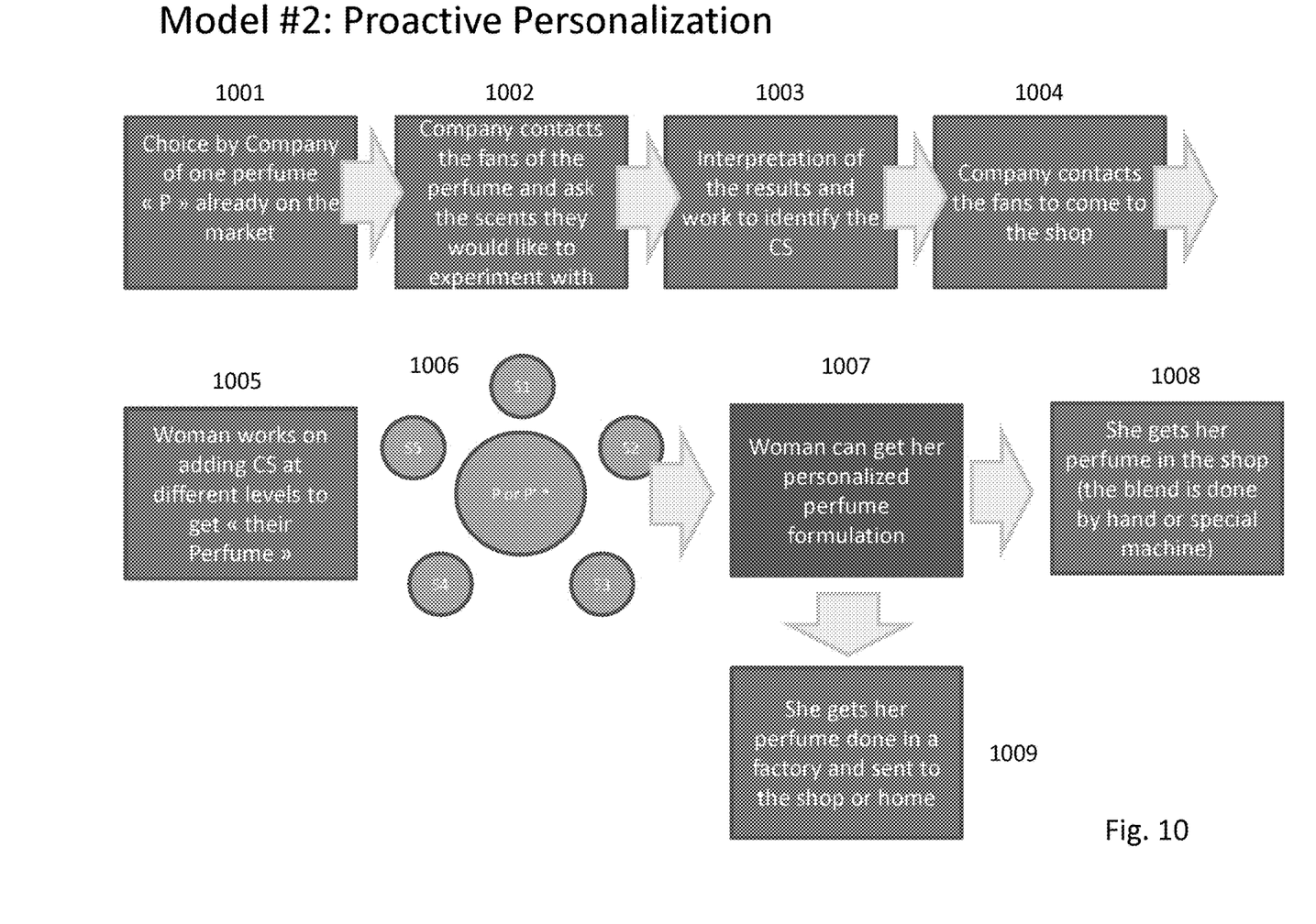
Figure 11:
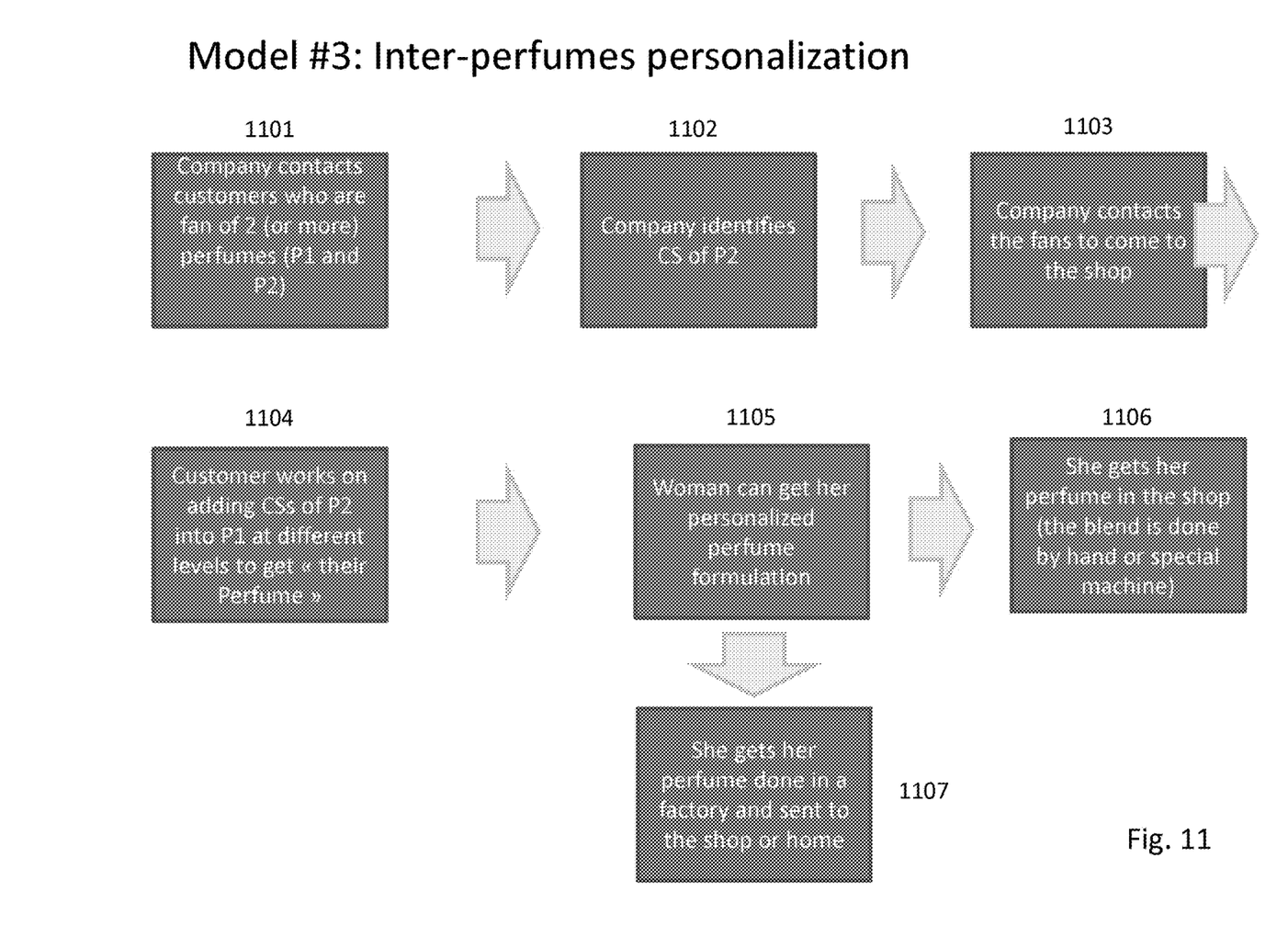

In some cases, notes are not equivalent in role. There is one scent that is central such that it will always be used. For instance:
One is a central and the others are used to change the smell of the central
The central note can be an existing perfume or simplified existing perfume and the others can be non-existing in the perfume market
The central note can be an existing perfume or simplified existing perfume and the others can be perfumes on the market The following example describes a scenario in which a combination of users is involved in the creation of a recipe. In this scenario, one person (P1) wishes to create a perfume that will suit her and also to another person (P2 (husband for instance)). In the solution, P1 will do a series of trials and quotations. P2 will do the same. The system will identify a scent which suits both P1 and P2, taking into account the following possibilities:

It will be hard that P1 and P2 like the exact same formulation.
P1 and P2 tend to like one of the six scents
P1 and P2 tend to like one combination of the six scents
Or it could be that P1 and P2 tend to dislike One of the six scents
P1 and P2 tend to dislike one combination of the six scents The Artificial Intelligence of the machine, knowing the tastes of P1, may be able to perform the following:

to propose to P2 scents, or combination of scents to test in priority
to propose to P2 to increase or decrease specific scents in his formula
to propose to P2 to start from a collection of specific formulation (it can one of the formulation of P1) and propose to P2 to work on The AI of the machine, knowing the tastes of P1, can also let P2 working on his own, and after a while, cross all the data and perform the following:

to propose to P2 scents, or combination of scents to test in priority
to propose to P2 to increase or decrease specific scents in his formula
to propose to P2 to start from a collection of specific formulation (it can one of the formulation of P1) and propose to P2 to work on FIGS. 9-11 show different exemplary models and scenarios in which the device 100 may be utilized for either creating a personalized perfume for a customer, or for developing a perfume product for a company.

FIG. 9 shows a first model, "Model #1", in which at step 901, a perfume company may select a perfume that is already on the market, and then in step 902, the company will determine characteristic scents (CS) already in the perfume. In the model shown in FIG. 9, there are five CSs, but is may be more or less. In step 903, the company may contact fans of the selected perfume and invite them to the location of the device 100 (such as a perfume retail store). In step 905, the customer uses the device 100 as described above by adding CSs at different levels to obtain a desired perfume scent combination. In step 907, the user can obtain their personalized perfume formulation based on the results of using the device 100. Then in either step 908 or 909, the customer may obtain a bottle of the personalized perfume by one of two methods: either at the store itself by hand or a special machine (step 908), or by sending the formulation to a remotely located factory so that the perfume can be sent to the customer via the store or by delivery directly to the customer's home.

FIG. 10 shows a second model "Model #2". Model #2 is similar to Model #2, except that instead of directly using the CSs based on what is actually used in the selected perfume (in step 1001) that is already in the market, the fans of the selected perfume are asked what scents they would like to experiment with in step 1002. In step 1003, the results are interpreted, either by an expert or a machine, to identify the CSs which will be used. Then steps 1004-1009 are similar to steps 905-909 above.

FIG. 11 shows a third model, "Model #3", for performing "inter-perfumes personalization." In this model, the company contacts customers who are fans of two or more perfumes P1 and P2 (step 1101), and the company identifies the CSs of perfume P2 (1102). The company then invites one or more of the fans of the two perfumes to use the device 100 (1103). Then in step 1104, the customer works on adding CSs of P2 into P1 at different levels to get a desired perfume scent. This may be done by ensuring that the P1 perfume is always dispensed from one of the containers in device 100. Then steps 1105-1107 are similar to steps 907-909 above.

Variations of the above models may be used as necessary. For instance, the company may contact a group of customers are fans of a perfume and ask the group members to work together with a combination of scents in the machine to obtain an consensus desired perfume. In that case, each group member may receive the personalized perfume via steps 907-909 above, or the company may use the results for testing and/or launching a new perfume for the general marketplace.

In another variation, the company may choose multiple predetermined scents, each being a simple perfume with top, middle, and base notes, and a customer can create blends of the multiple scents to obtain a personalized perfume. In this variation, the quality of the final perfume depends on the quality of each of the predetermined scents, which may help a company stand out from other scent-makers.

In another variation, instead of adding just the CSs from a selected perfume on the market, a scent note may be added to each of the CSs in each container, where the scent notes are predetermined to fit well with the selected perfume.

In another variation, an expert (guru) may be involved in the models described above. Such an expert does not even need to be co-located with the customer, but just needs to be able to reproduce the creation by the user based on using the same scents at the same levels as the user. After the expert reproduces the customer's creating, the expert can provide advice for proposed variations, which the customer then uses to produce a new customized perfume formulation.

Alternatively, instead of a human expert, a machine may be able to provide advice for a proposed variation to a customer's personalized perfume by comparing the customer's initial creation to perfumes created by other users. For instance, by using tables that link the differences between different users' creations, the machine is able to deduce a proposed variation to the user, which the customer may then use to produce a new customized perfume formulation.

In another variation, the company may select a "pre-perfume," which is a high-quality perfume that is not yet finalized for selling on the market. CSs from the pre-perfume are used similar to any of the models above. However, in this case, since there are no identified "fans" of the perfume available yet, the customers who are invited to use the device 100 may be contacted by any number of characteristics. For instance, they may be invited based on their tastes in perfumes similar to the pre-perfume, or they may be invited based on their personal information, such as age and gender.

In another variation, a company may use multiple groups to find a perfume formulation that is ideal for the marketplace. In this case, a similar set of CSs may be given to different groups, and each group will make their own consensus perfume creation. All the creations may be formed into a collection of perfumes to be launched to market. Or, all creations may be analyzed to find a "mean" perfume for launching to market that reflects an average of the characteristics of each of the separate creations.

In another variation, both the company and the customer/client may combine any precious scents that are available separately to them in to the device 100 to create one or more preferred perfume formulations for either the customer's personal use or for the company to launch to market.

The device 100 and the processes described above are not limited to be used for scents in perfumes, but can be used for scents in any number of applications, such as food, clothing, hair products, air fresheners, and others.

The principles, representative embodiments, and modes of operation of the present disclosure have been described in the foregoing description. However, aspects of the present disclosure which are intended to be protected are not to be construed as limited to the particular embodiments disclosed. Further, the embodiments described herein are to be regarded as illustrative rather than restrictive. It will be appreciated that variations and changes may be made by others, and equivalents employed, without departing from the spirit of the present disclosure. Accordingly, it is expressly intended that all such variations, changes, and equivalents fall within the spirit and scope of the present disclosure, as claimed.

What is claimed is:

1. A scent dispensing device, comprising:
    a plurality of containers, each containing a different scent ingredient;
    a driving system configured to separately cause each of the plurality of containers to dispense a quantity of a respective scent ingredient;
    a delivery system configured to transport any dispensed quantities from the scent containers to a common receiving area for dispensing onto to a single medium,
    wherein the driving system includes an electric motor that drives a gearhead which pushes a piston to dispense a quantity of a scent in a respective container, and
    an encoder is coupled to the electric motor and is configured to count step movements of the gearhead, wherein the electric motor controls the dispensing of the quantity of the scent based on the count detected by the encoder.

2. The scent dispensing device according to claim 1, wherein a dispensed quantity of each unitary drop of the respective scent ingredient is less than or equal to 2 μL.

3. The scent dispensing device according to claim 1, wherein a dispensed quantity of each unitary drop of the respective scent ingredient is less than or equal to 4 μL.

4. The scent dispensing device according to claim 1, wherein a dispensed quantity of each unitary drop of the respective scent ingredient is less than or equal to 10 μL.

5. The scent dispensing device according to claim 1, wherein a total quantity of a dispensed quantity of the respective scent ingredients onto the single medium is less than 200 μL.

6. The scent dispensing device according to claim 1, wherein the encoder is configured to detect a total quantity of the scent dispensed by a respective container based on an amount of step movements that have been performed by the gearhead.

7. The scent dispensing device according to claim 1, wherein a movement of the piston causes an amount of a scent liquid to be pushed through a capillary which is connected to a tube which leads to the common receiving area.

8. The scent dispensing device according to claim 7, wherein an internal diameter of the tube is between 0.5 mm and 3 mm.

9. The scent dispensing device according to claim 7, wherein an internal diameter of the tube is between 0.7 mm-1 mm.

10. A system comprising:
    a user terminal configured to receive an input of a recipe to form a scent based on one or more quantities of different scents chosen from a plurality of different scent ingredients; and
    a scent dispensing device that includes:
        a communication interface configured to receive the recipe from the user terminal,
        a plurality of containers, each containing one of the plurality of different scent ingredients;
    wherein the scent dispensing device is configured to separately cause the plurality of containers to dispense a quantity of a respective scent ingredient onto a single medium according to the recipe,
    wherein the scent dispensing device includes an electric motor that drives a gearhead which pushes a piston to dispense a quantity of a scent in a respective container, and
    an encoder is coupled to the electric motor and is configured to count step movements of the gearhead, wherein the electric motor controls the dispensing of the quantity of the scent based on the count detected by the encoder.

11. The system according to claim 10, wherein after the plurality of containers dispense the quantity of a respective scent ingredient onto the single medium according to the recipe, a user interface is configured to allow a user to revise the recipe.

12. The system according to claim 10, wherein after the plurality of containers dispense the quantity of a respective scent ingredient onto the single medium according to the recipe, a user interface is configured to allow a user to store the recipe into a memory.

13. The system according to claim 10, wherein after the plurality of containers dispense the quantity of a respective scent ingredient onto the single medium according to the recipe, a user interface is configured to allow a user to request a bottle of perfume having a predetermined volume be created according to the recipe.

14. The system according to claim 10, wherein after the plurality of containers dispense the quantity of a respective scent ingredient onto the single medium according to the recipe, a user interface is configured to allow a user to provide feedback regarding the user's opinion of a created scent.

* * * * *

UNITED STATES PATENT AND TRADEMARK OFFICE
CERTIFICATE OF CORRECTION

| | |
|---|---|
| PATENT NO. | : 11,040,122 B2 |
| APPLICATION NO. | : 16/151411 |
| DATED | : June 22, 2021 |
| INVENTOR(S) | : Henri Samain et al. |

It is certified that error appears in the above-identified patent and that said Letters Patent is hereby corrected as shown below:

In the Specification

In Column 3, Line 9, please delete "pt." and insert -- µL. --;

In Column 5, Line 38, please delete "Utlizing" and insert -- Utilizing --; and

In Column 6, Line 8, please delete "it can ask to activate functions like to" and insert -- it can ask to activate functions like --.

Signed and Sealed this
Twenty-ninth Day of March, 2022

Drew Hirshfeld
*Performing the Functions and Duties of the*
*Under Secretary of Commerce for Intellectual Property and*
*Director of the United States Patent and Trademark Office*